(12) United States Patent
Chalmers et al.

(10) Patent No.: US 7,505,556 B2
(45) Date of Patent: *Mar. 17, 2009

(54) X-RAY BACKSCATTER DETECTION IMAGING MODULES

(75) Inventors: Alex Chalmers, Norwood, MA (US); Louis W. Perich, Londonderry, NH (US); Peter Rothschild, Boston, MA (US); William John Baukus, Nashua, NH (US)

(73) Assignee: American Science and Engineering, Inc., Billerica, MA (US)

( * ) Notice: Subject to any disclaimer, the term of this patent is extended or adjusted under 35 U.S.C. 154(b) by 38 days.

This patent is subject to a terminal disclaimer.

(21) Appl. No.: 11/608,957

(22) Filed: Dec. 11, 2006

(65) Prior Publication Data

US 2007/0269005 A1 Nov. 22, 2007

Related U.S. Application Data

(63) Continuation-in-part of application No. 11/238,719, filed on Sep. 29, 2005, now Pat. No. 7,218,704, which is a continuation of application No. 10/442,687, filed on May 21, 2003, now Pat. No. 7,099,434, which is a continuation of application No. 10/330,000, filed on Dec. 26, 2002, now abandoned.

(60) Provisional application No. 60/424,357, filed on Nov. 6, 2002.

(51) Int. Cl.
*G01N 23/04* (2006.01)
(52) U.S. Cl. .................... 378/57; 378/87; 250/358.1
(58) Field of Classification Search .............. 378/57, 378/87; 250/358.1
See application file for complete search history.

(56) References Cited

U.S. PATENT DOCUMENTS

| 3,569,708 | A | 3/1971 | Weinbaum et al. | 250/83.3 |
|---|---|---|---|---|
| 3,868,506 | A | 2/1975 | Osigo | 250/278 |
| RE28,544 | E | 9/1975 | Stein et al. | 250/369 |
| 3,928,765 | A | 12/1975 | Teller | 250/272 |
| 4,047,029 | A | 9/1977 | Allport | 250/273 |
| 4,052,617 | A | 10/1977 | Garrett et al. | 250/360 |
| 4,342,914 | A | 8/1982 | Bjorkholm | 378/99 |
| 4,458,152 | A | 7/1984 | Bonora | 250/353 |

(Continued)

FOREIGN PATENT DOCUMENTS

WO WO 00/33060 6/2000

OTHER PUBLICATIONS

U.S. Appl. No. 09/305,417, filed May 5, 1999, Swift et al.

*Primary Examiner*—Chih-Cheng G Kao
(74) *Attorney, Agent, or Firm*—Bromberg & Sunstein LLP

(57) ABSTRACT

An inspection system based upon an imaging enclosure characterized by an enclosing body, or skin. A source of penetrating radiation and a spatial modulator for forming the penetrating radiation into a beam, are both concealed entirely within the body of an enclosure such as a shipping container for convenient operational deployment. Multiple modules, such as for providing power and for enclosing an operator console may be coupled to the imaging enclosure. An image is formed of the contents of the object based in part on the scatter signal and the relative motion signal. A detector, which may be separate or part of the scatter detector module, may exhibit sensitivity to decay products of radioactive material.

4 Claims, 6 Drawing Sheets

U.S. PATENT DOCUMENTS

| | | | |
|---|---|---|---|
| 4,768,214 A | 8/1988 | Bjorkholm | 378/87 |
| 4,799,247 A | 1/1989 | Annis et al. | 378/87 |
| 4,864,142 A | 9/1989 | Gomberg | 250/390.04 |
| 4,884,289 A | 11/1989 | Glockmann et al. | 378/57 |
| 4,974,247 A | 11/1990 | Friddell | 378/90 |
| 5,002,397 A | 3/1991 | Ingrum et al. | 356/407 |
| 5,014,293 A | 5/1991 | Boyd et al. | 378/197 |
| 5,022,062 A | 6/1991 | Annis | 378/86 |
| 5,065,418 A | 11/1991 | Bermbach et al. | 378/57 |
| 5,091,924 A | 2/1992 | Bermbach et al. | 378/57 |
| 5,132,995 A | 7/1992 | Stein | 378/56 |
| 5,179,581 A | 1/1993 | Annis | 378/57 |
| 5,181,234 A | 1/1993 | Smith | 378/87 |
| 5,224,144 A | 6/1993 | Annis | 378/146 |
| 5,253,283 A | 10/1993 | Annis et al. | 378/100 |
| 5,302,817 A | 4/1994 | Yokota et al. | 250/214 |
| 5,313,511 A | 5/1994 | Annis et al. | 378/87 |
| 5,349,191 A * | 9/1994 | Rogers | 250/363.02 |
| 5,391,879 A | 2/1995 | Tran et al. | 250/370.09 |
| 5,591,462 A | 1/1997 | Darling et al. | 425/173 |
| 5,629,966 A | 5/1997 | Dykster et al. | 378/57 |
| 5,638,420 A | 6/1997 | Armistead | 378/57 |
| 5,692,028 A | 11/1997 | Geus et al. | 378/57 |
| 5,692,029 A | 11/1997 | Husseiny et al. | 378/88 |
| 5,764,683 A | 6/1998 | Swift et al. | 378/57 |
| 5,838,759 A | 11/1998 | Armistead | 378/57 |
| 5,903,623 A | 5/1999 | Swift et al. | 378/57 |
| 5,940,468 A | 8/1999 | Huang et al. | 378/57 |
| 6,067,344 A | 5/2000 | Grodzins et al. | 378/117 |
| 6,094,472 A | 7/2000 | Smith | 378/86 |
| 6,249,567 B1 | 6/2001 | Rothschild et al. | 378/88 |
| 6,269,142 B1 | 7/2001 | Smith | 378/57 |
| 6,292,533 B1 | 9/2001 | Swift et al. | 378/57 |
| 6,424,695 B1 | 7/2002 | Grodzins et al. | 378/87 |
| 6,727,506 B2 | 4/2004 | Mallette | 250/394 |
| 7,099,434 B2 * | 8/2006 | Adams et al. | 378/57 |
| 7,218,704 B1 * | 5/2007 | Adams et al. | 378/57 |
| 2002/0185612 A1 | 12/2002 | Chalmers et al. | 378/87 |
| 2003/0016790 A1 | 1/2003 | Grodzins et al. | |

* cited by examiner

X-RAY BACKSCATTER DETECTION IMAGING MODULES

The present application is a continuation-in-part application of copending U.S. Ser. No. 11/238,719, filed Sep. 29, 2005, which is a continuation application of U.S. Ser. No. 10/442,687, filed May 21, 2003, now issued as U.S. Pat. No. 7,099,434, which was a continuation-in-part of U.S. Ser. No. 10/330,000, filed Dec. 26, 2002, and claimed priority from U.S. Provisional Application Ser. No. 60/424,357, filed Nov. 6, 2002, as does the present application. All of the foregoing applications are incorporated herein by reference.

TECHNICAL FIELD

The present invention relates to devices and methods for remote sensing and imaging of items concealed, typically on persons or within enclosed vehicles, by using scattered x-rays and passive sensing of gamma rays or neutrons from within a readily transportable enclosure.

BACKGROUND OF THE INVENTION

X-rays are currently employed for the inspection of cargo containers, including motor vehicles, freight pallets, etc. Current technology, however, typically requires that some structure associated with the inspection system be disposed on either side of the inspected object. Thus, for example, a source of x-rays may be disposed distally with respect to the inspected object while a detection system disposed proximally to the inspected object characterizes the x-rays which have traversed the inspected object. In other modes of x-ray inspection, described in U.S. Pat. No. 6,292,533, issued Sep. 18, 2001 and incorporated herein by reference, a source of penetrating radiation is mounted on a moveable bed which is driven by a stationary cargo container, while a boom extends either a detector or a beam stop to the distal side of the cargo container. Current technology, in summary, requires that the inspected objects or persons either be moved through an inspection system or interposed between a proximal examining component and a distal examining component, one including a source and the other including a detector.

An effective means, however, is desirable for non-intrusively examining personnel as well as the interior of vehicles, cargo containers, or other objects. In particular, with respect to cargo enclosures, it is desirable to detect the presence of people, potential contraband, threats, or other items of interest, without imposing the requirements and constraints of current systems. Combining such an examination with passive sensing of radioactive or fissile material would also be advantageous.

SUMMARY OF THE INVENTION

In accordance with one aspect of the invention, in one of its embodiments, there is provided an inspection system for inspecting persons or objects, or objects carried on persons. The object of inspection may also be cargo or a vehicle of any sort. The inspection system has an enclosed conveyance, such as a van or other vehicle, characterized by an enclosing body. Additionally, the system has a source of penetrating radiation contained entirely within the body of the conveyance for generating penetrating radiation, along with a spatial modulator for forming the penetrating radiation into a beam for irradiating the object with a time-variable scanning profile. A detector module, also contained entirely within the body of the conveyance, is provided for generating a scatter signal based on penetrating radiation scattered by contents of the object, while a proximity sensor generates a relative motion signal based on a relative disposition of the conveyance and the inspected object. Finally, the system has a controller for ascertaining a specified characteristic of the scattered radiation. Additionally, an image generator may be provided for forming the signal into an image of the contents of the object based in part on the scatter signal and the relative motion signal.

In accordance with further embodiments of the invention, the conveyance may include a vehicle capable of road-travel. The source of penetrating radiation may include an x-ray tube, more particularly, an x-ray tube emitting radiation at energies below approximately 250 keV. The source of penetrating radiation may include a rotating chopper wheel emitting radiation to one or both sides of the enclosed conveyance.

In accordance with yet further embodiments of the invention, the proximity sensor may be chosen from the group of sensors including radar, ultrasound, optical, laser, and LIDAR sensors. A detector, which may be separate or the same as one of the scatter detectors, may also exhibit sensitivity to decay products of radioactive or fissile material, and may be sensitive, particularly, to neutrons or gamma rays.

BRIEF DESCRIPTION OF THE DRAWINGS

The foregoing features of the invention will be more readily understood by reference to the following detailed description taken with the accompanying drawings.

DETAILED DESCRIPTION OF PREFERRED EMBODIMENTS

Figure 1:
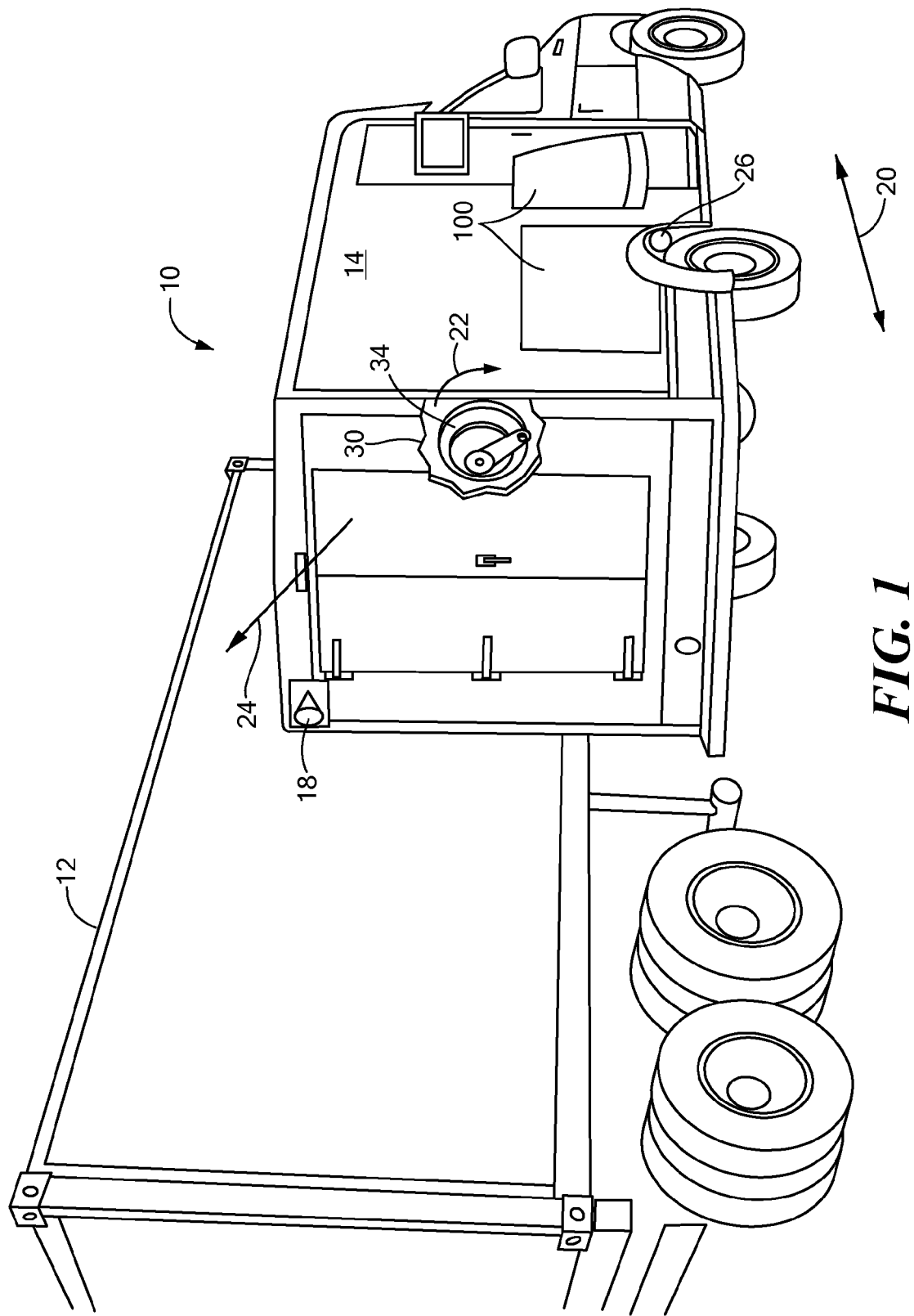
FIG. 1 is a perspective view, cutaway in part, of a mobile cargo inspection system deployed on a truck capable of on-road travel and scanning of an enclosure such as a vehicle or cargo container while one or both of the inspection system and enclosure are in motion, in accordance with preferred embodiments of the present invention.

As used in this description and in the appended claims, a "cargo container" is a receptacle for the storage or transportation of goods, and includes freight pallets as well as vehicles, whether motorized or drawn, such as automobiles, the cab and trailer of a truck, railroad cars or ship-borne containers. The term "cargo container," as used herein, further includes the structures and components of the receptacle.

The invention described herein serves to characterize materials which may be contained within a cargo container and thus not readily susceptible to visual scrutiny, or, alternatively, may be carried on the person of a human or on another animate subject. The characteristics of a material which might be the object of non-invasive inspection and which lend themselves to detection using the device and method taught by the invention include, but are not limited to, electron density, atomic number, mass density, linear dimensions and shape. These characteristics are unveiled by taking advantage of the various physical processes by which penetrating radiation interacts with matter.

Penetrating radiation refers to electromagnetic radiation of sufficient energy per photon to penetrate materials of interest to a substantial and useful degree and include x-rays and more energetic forms of radiation. The interaction of such radiation with matter can generally be categorized as either scattering or absorption processes. Both types of process remove x-ray photons from a collimated (i.e., directional) beam; scattering processes do so by deflecting photons into new directions (usually with loss of energy), while absorption processes simply remove photons from the beam.

Description of the rudiments of a mobile inspection system is to be found in U.S. Pat. No. 5,764,683, issued Jun. 9, 1998, and incorporated herein by reference. As used in this description and in any appended claims, the term "source" is used in a broad sense to encompass the entirety of the apparatus used to generate a beam of penetrating radiation that is used to irradiate the object under inspection. The source is taken to include the generator of penetrating radiation (the "source", in the narrow sense) which may include an x-ray tube or a radio-isotope. It is, furthermore, to be understood that the term "source" as used herein and in any appended claims, and as designated generally by numeral 30 in the drawings, refers to the entirety of the apparatus used to generate beam 24, and may have internal components that include, without limitation, apertures, choppers, collimators, etc.

Scatter imaging in which the x-rays scattered by a material (typically in a generally backward direction) are employed offers several unique inspection capabilities and operational features. Scatter imaging allows images to be obtained even when the imaged object is accessible from only one side. Moreover, since the scatter signal falls off quite rapidly with increasing depth into the object, backscatter images effectively represent a "slice" of the object characteristic of the side nearest to the x-ray source, thereby reducing problems of image clutter that may confound transmission images. The Compton effect, which dominates x-ray scatter in the energy range typically employed in accordance with the present invention, dominates the interaction of x-rays with dense low-atomic-number (low-Z) materials. Narcotic drugs tend to produce the bright signatures in a backscatter image, as do organic explosives, making backscatter imaging a useful imaging modality for bomb or drug detection. Finally, alignment requirements of the x-ray beam with detectors or collimation devices are less exacting than for transmission imaging thereby enabling rapid deployment in a wide range of inspection scenarios.

Flying-spot technology makes possible the acquisition of images using detectors specifically positioned to collect the scattered x-rays. In a typical flying-spot system, a thin "pencil beam" of x-rays is rapidly and repetitively swept through a source-centered, vertically-oriented "fan" of beam paths that are arranged to intercept the object under inspection. At the same time, the object is moved at a constant, slower speed along a path perpendicular to the fan, on a horizontally moving conveyor belt for example. In this way, the pencil beam is made to traverse the object in point-by-point raster fashion, and the entire object is scanned as it passes through the fan plane over a period ranging from a few seconds to a few minutes depending upon the length of the object.

Although the total scan time may be seconds to minutes in duration, the actual exposure time of any part of the scanned object is only the brief time it takes for the pencil beam to sweep across a given pixel. That exposure time is typically in the range of microseconds, depending on the design and the application, and yields an entrance exposure to the scanned object that constitutes a low dose to the object also means that there is little radiation available to scatter into the environment, so the doses to operators and other bystanders is correspondingly low.

Referring now to FIG. 1, various embodiments of this invention make use of systems in which detectors are mounted on a mobile platform 10, or conveyance, typically capable of road travel, that traverses a large object to be inspected such as a vehicle or a cargo container 12. Conveyance 10 is characterized by an enclosure 14, here, the skin of a van, shown, in cutaway view, to enable depiction of other components of an inspection system. The conveyance can have many alternate embodiments, including but not limited to gasoline, diesel, electric, propane, battery, fuel-cell, or hydrogen-powered motor vehicles (including vans, trucks, or similar), tracked vehicles, sleds, trailers, cranes, or other equipment that can be put into motion, preferably self-propelled, but also including vehicles tethered and pulled such as under electric power.

Contained within enclosure 14 of conveyance 10 is a source 30 including x-ray tube 32 (shown in FIG. 3) and chopper 34. In accordance with preferred embodiments of the invention, source energies are typically below 250 keV, thus the chopper 34 may be smaller than employed in current systems in which higher-energy x-rays are employed. Chopper 34 may be a rotating perforated hub, or a wheel with transmitting spokes, or any number of means, known in the art, for generation of flying spot beams that lie, typically, in a plane approximately orthogonal to the direction of motion of 20. The x-ray tube 32 depicted in FIG. 3, by way of example, is a panoramic-style x-ray tube that is capable of wide-angle beam generation and additionally may be rotatable to allow scanning on either side of conveyance 10. Rotating hoop 34, with apertures 36 and 38, emits a pencil beam 24, thereby enabling inspection of objects, possibly on either side of the conveyance, herein referred to as "bilateral" inspection. However, all sources are encompassed within the scope of the present invention when employed in the manner described in the present description. The x-ray source and detectors may be oriented to permit scanning from the conveyance's "driver's side", "passenger's side", or both sides simultaneously.

Figure 3:
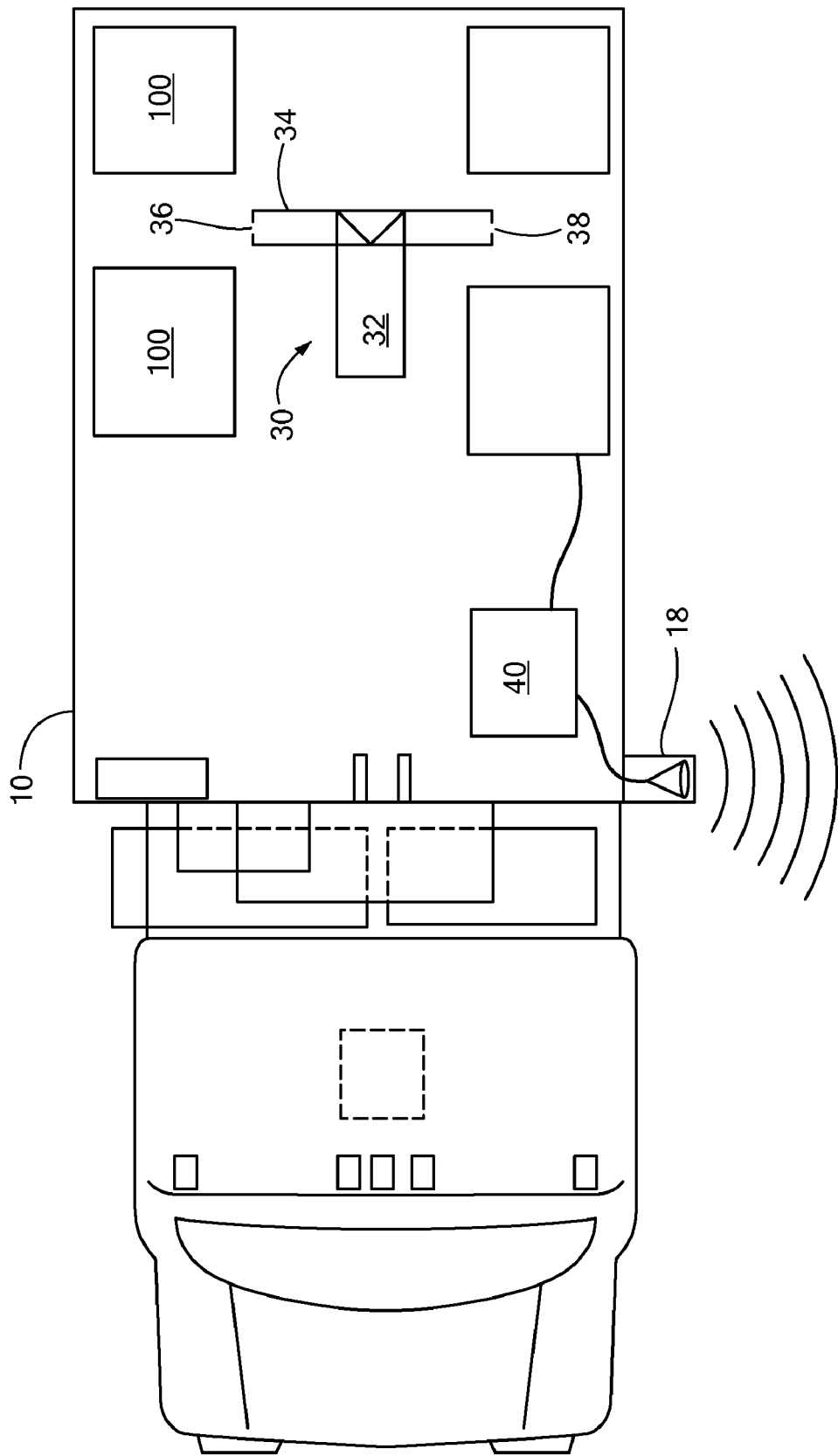
FIG. 3 is a schematic representation of an inspection vehicle, in accordance with embodiments of the present invention, providing inspection capability to either side of the vehicle.

Various means are known in the art for mechanically or electronically sweeping a beam of penetrating radiation, including, for example, the rotating chopper wheel 34 depicted in FIG. 3 or electronic scanning is described in detail, for example, in U.S. Pat. No. 6,421,420, issued Jul. 16, 2002, which is incorporated herein by reference. In embodiments employing a mechanical rotating chopper wheel 34, as the chopper wheel rotates in the direction of arrow 22, penetrating radiation 24 emitted from the target of x-ray tube 32 passes successively through a plurality (typically, three or four) of channels. Wheel 34 is fabricated from a material, typically lead, that blocks transmission of x-rays except through apertures 36. X-rays 24 emerge from the currently illuminated channel as a pencil beam that is swept across object 12 undergoing inspection as wheel 34 rotates. The dimensions of the beam 24 typically govern the resolution of a system such as the one depicted. Aperture 36 may have various shapes, and may be circular or rectangular, and may be more specifically tailored. Other x-ray generation approaches may be used to produce a similar sweeping pencil beam, such as spinning discs with elongated slits, wheels with hollow spokes, are alternate embodiments.

Detector modules 100 are carried by conveyance 10 and typically enclosed within enclosing body 14 and concealed from view from outside the conveyance. They may also be carried outside the conveyance for particular applications within the scope of the present invention. Detector modules contain detectors for detecting penetrating radiation from source 30 that has interacted with, and scattered from, contents of the inspected object 12.

The source of scattering may be characterized as anomalous for the nature of the person or item being scanned. Thus, a person 50 (shown in FIG. 2) carrying explosives may be detected on the basis of locally enhanced x-ray scatter. A specified characteristic of the scatter, such as a localization or particular disposition with respect to the inspected object, may be ascertained in order to determine threat levels of the object.

Detector modules 100 may also be sensitive both to emission naturally emitted by threat materials, as further described, for example, in copending U.S. patent application Ser. No. 10/156,989, filed May 29, 2002, entitled "Detectors for X-Rays and Neutrons," which is incorporated herein by reference. In accordance with various embodiments of the present invention, a detector is employed of the type having high efficiency for detecting thermal and epi-thermal (intermediate energy, typically $1\text{-}10^4$ eV) neutrons. The detector uses the scintillator $Gd_2O_2S$, commonly known, and referred to herein, as "gadox," to stop both neutrons and the photons. X-ray-induced scintillations from the gadox in the visible portion of the spectrum are then detected, typically by photomultipliers or photodiodes. Alternative scintillators, such as LiF, for example, with high cross sections for detecting thermal and epithermal neutrons are also within the scope of the present invention.

Separate, large-area detectors are deployed adjacent to the beam plane on the x-ray source side of the scanned object, and with their active surfaces oriented toward the scanned object. These detectors need only provide a large solid angle for collection of scattered radiation; no critical alignments are required. In this location these detectors respond to x-rays which are scattered generally back toward the source from the object.

FIG. 3 shows a schematic top view of another embodiment of the invention that may advantageously be employed for the inspection of objects disposed to either side of the inspecting conveyance.

In accordance with the present invention, various inspection modalities currently in use for detection of contraband materials may additionally be used for finding fissionable material in the containers they examine. Some methods are passive; i.e., the emission of neutrons or gamma rays from radioactive materials may be signatures for an alert. Several methods for carrying out such passive measurements are described in copending U.S. Provisional Application, Ser. No. 60/396,034, filed Jul. 15, 2002, and incorporated herein by reference. Other methods are active; i.e., penetrating radiation irradiates a container thereby exciting fluorescence of the fissile material and the characteristic x-rays of uranium or plutonium produce an alert signal.

Inspection of object 12 may be conducted by an operator disposed within conveyance 10, or, alternatively, by a remotely disposed operator. For inspection, object 12 may be maintained in a stationary condition, with conveyance 10 traversing the object along direction 20 (forwards or backwards), alternatively, inspection may be conducted while both conveyance 10 and inspected object 12 are in motion. In yet another mode, referred to as a "portal mode," the system is stationary and the object of inspection is conveyed past the system. Where the object of inspection is a person, the person may be required to walk past the conveyance slowly, preferably in both directions, so that both sides of the person can be subjected to search.

Referring further to FIG. 3, the x-ray beams in x-ray inspection systems typically sweep, as by rotation of chopper wheel 34, through the inspection volume during a large fraction of the operating time. During the remaining fraction of each sweep cycle there are essentially no source x-rays striking the target container. Thus, during the time of source quiescence, the detectors are only counting background.

In a preferred embodiment, particularly useful for lower energy (140 keV-160 keV) x-ray systems, the output from backscatter detectors 100 are switched to a pulse counting circuit during the fraction of the operating cycle during which the source of x-ray irradiation is off. During this period, individual neutrons or gamma rays can be detected and analyzed. The efficiency of the backscatter detectors of an x-ray inspection system for detecting neutrons or gamma ray has been discussed above.

Referring only to gamma ray detection for purposes of illustration, the 186 keV gamma rays are emitted in 53% of the decays of $^{235}U$ but only a thin layer of the bulk uranium is accessible since the mean free path of 186 keV gammas in uranium is only 0.36 mm. Still, every square centimeter of 10% enriched uranium will emit~two thousand 186 keV gamma photons per second, giving rise to a count of 2,000× 0.004=8 counts for every square centimeter of surface area of uranium that faces the detectors. A 1" cube of uranium (weighing~¾ pounds) would signal its presence with~50 counts in the 0.2 second off-period of the inspection. A signal of this magnitude is easily discriminated. The signal strength is further increased by increasing detection efficiency, enlarging the detectors, and increasing the off-time of the sweeping x-ray beam.

In a "stationary mode," both the system and the object being scanned are stationary, and a vehicle-mounted x-ray scanning method, configured as a part of the system itself, is employed to create in effect both horizontal and vertical scanning to generate a backscatter x-ray image. Such methods may include the use of an x-y translation stage, electronically-steered x-ray sources (as described, for example, in U.S. Pat. No. 6,421,420, or other means.

Figure 4:
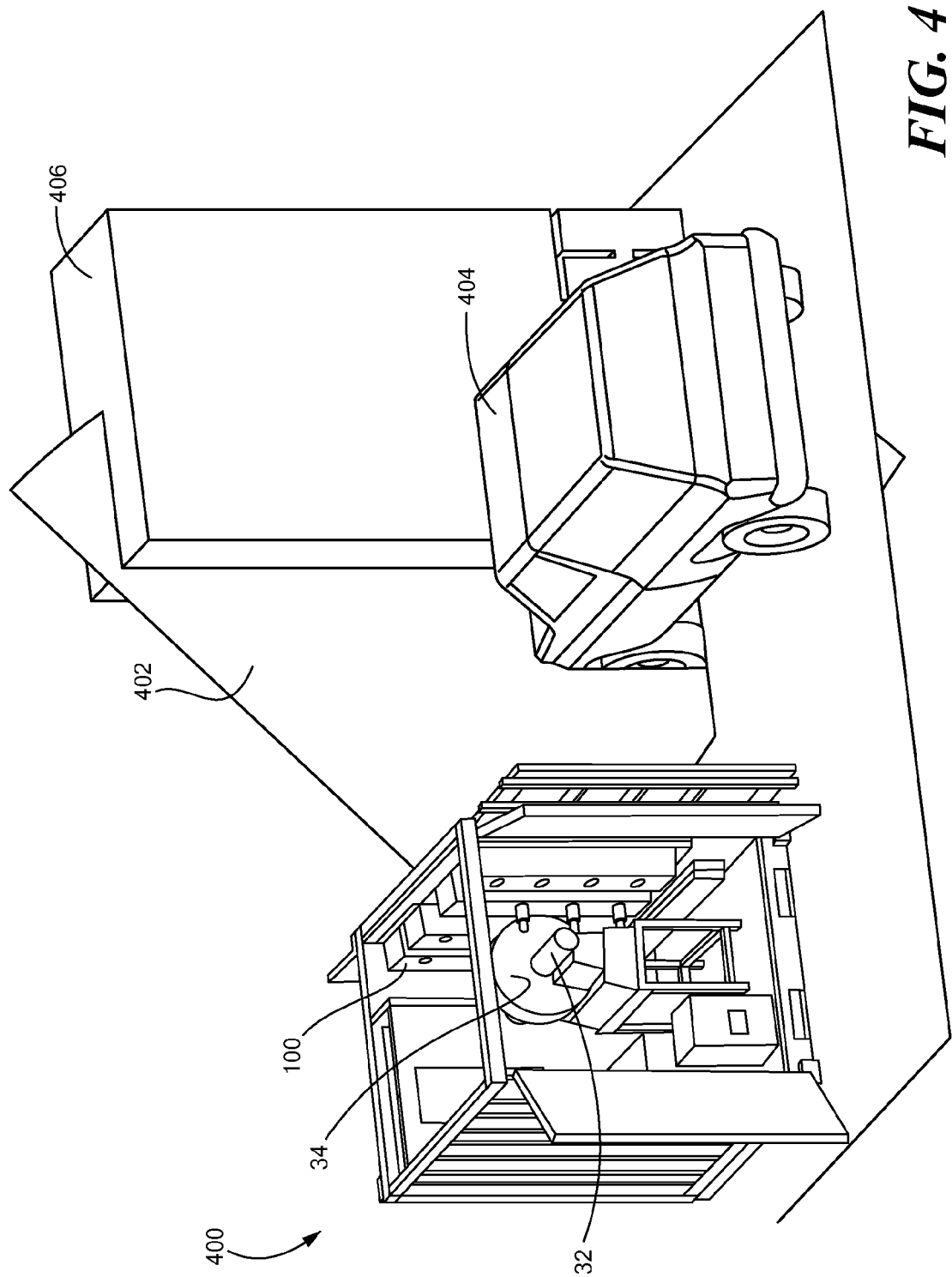
FIG. 4 is schematic representation of an embodiment of the invention in which a source of penetrating radiation and detection modules are concealed within a container.

In other embodiments of the invention, now described with reference to FIG. 4, a source of penetrating radiation, including x-ray tube 32 and chopper 34, as well as scatter detector modules 100 are included within a static imaging module 400, shown with its top panel removed for convenience of depiction. In practice, it is advantageous that all components of the x-ray inspection system be concealed within imaging module 400, so as not to be discernable from outside the module. Imaging module 400 is advantageously a standard shipping container (such as a TRICON triple container, standardized for ground and air transport), and may contain attachment points for helicopter deployment to a location where it remains static for some duration.

The x-ray beam is swept in a vertical swath, depicted schematically by the partial plane designated by numeral 402. An inspected object 404, exemplified here by a vehicle, is scanned by x-rays as it traverses plane 402. X-rays scattered by object 404 are detected by detector modules 100, which x-rays transmitted, or forward-scattered, through object 404 and detected by transmission or forward-scatter detectors (not shown) disposed within a forward-detection housing 406.

Figure 5:
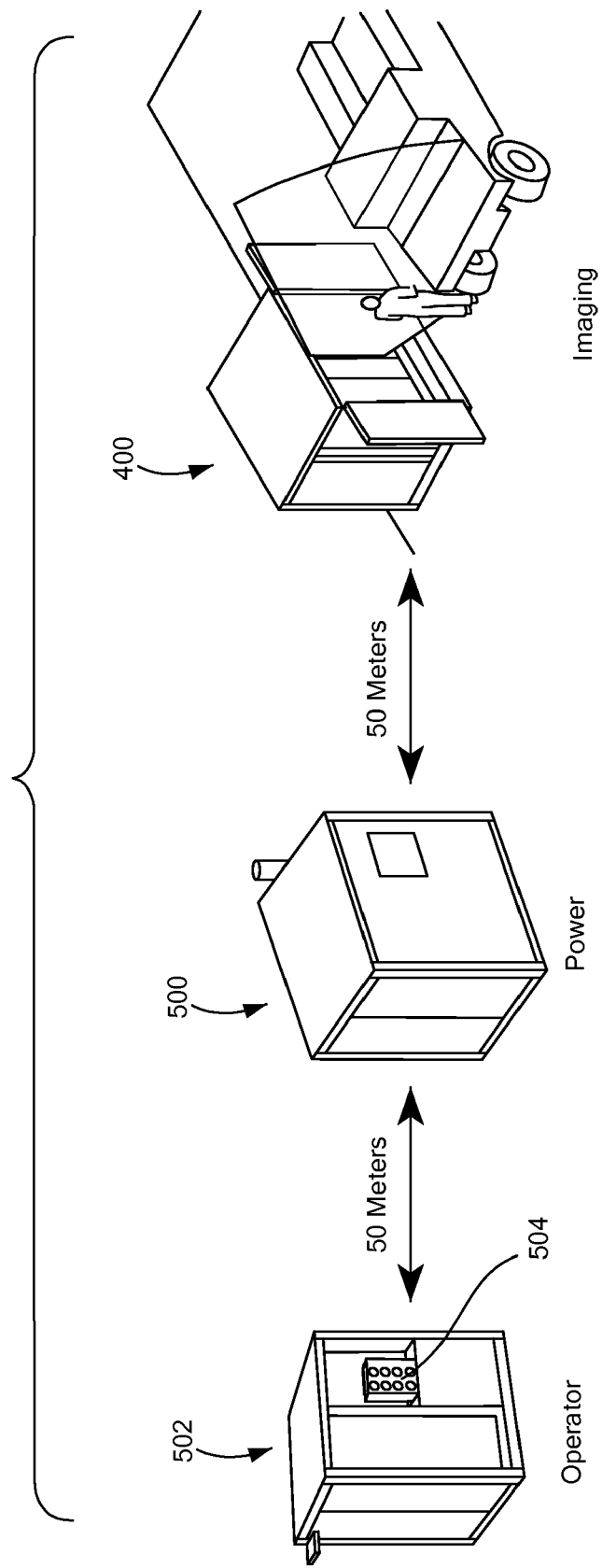
FIG. 5 shows a modular configuration of an inspection system in which distinct functional components of the inspection system are disposed within coupled modules.

In accordance with preferred embodiments, imaging module 400 is deployed operationally in conjunction with one or more other containers, as shown in FIG. 5, such as power module 500 and operator module 502, containing an operator console 504, all intercoupled by power and telemetry connections for coupled operation.

Figure 7:
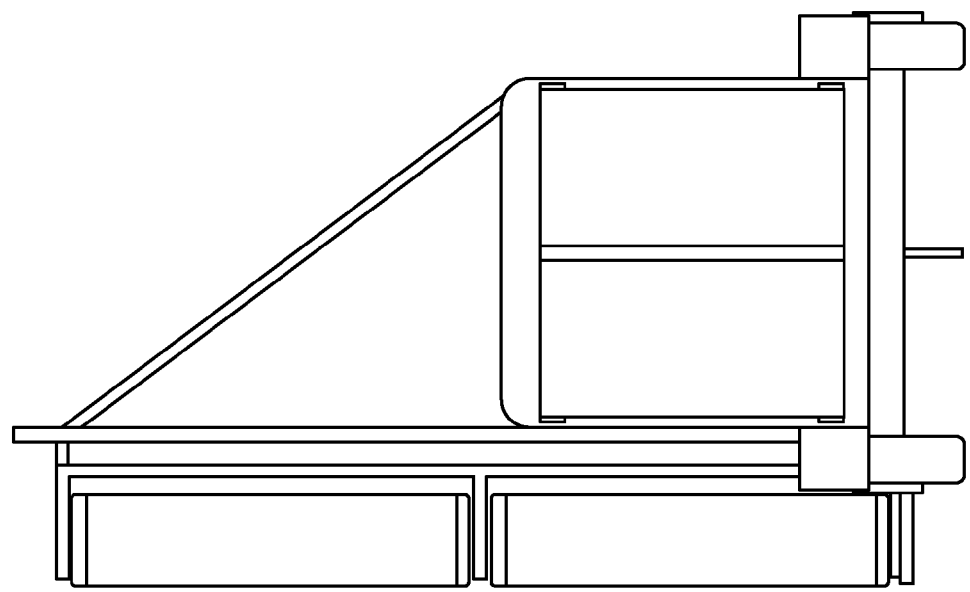
FIG. 7 is a rear view of the trailer-borne inspection system of FIG. 6.
Figure 6:
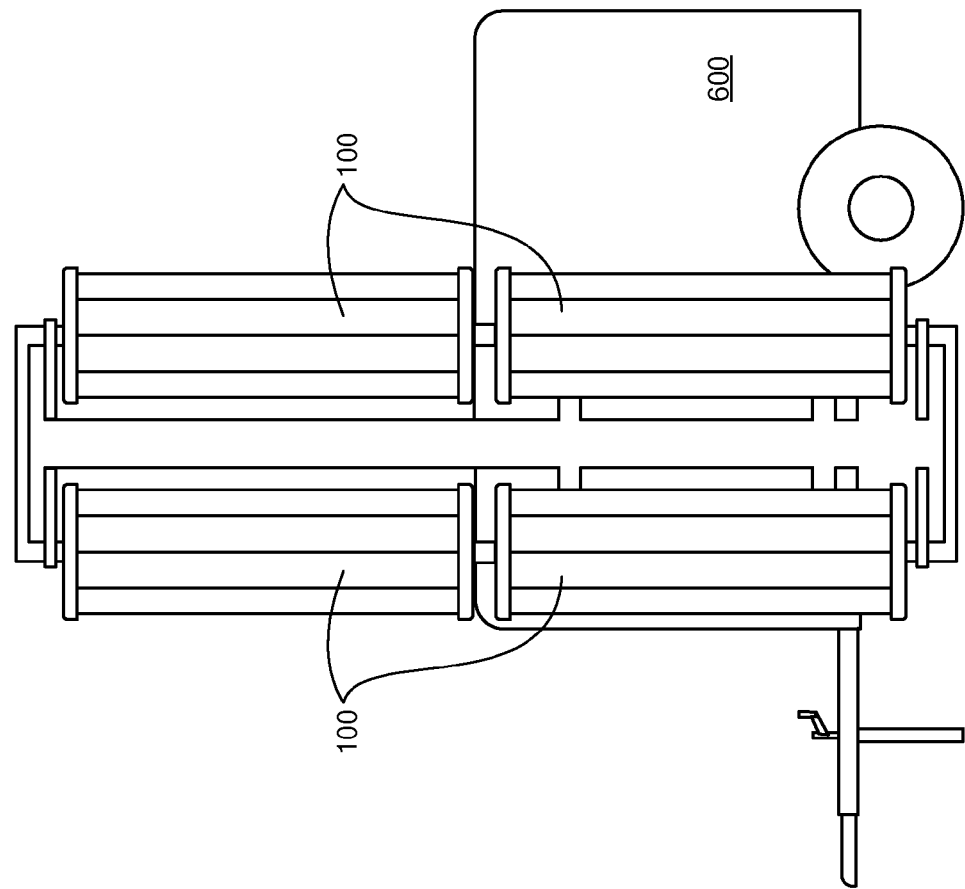
FIG. 6 is a side view of an inspection system deployed from within a self-contained trailer.

FIG. 6 shows a side view of an embodiment of the invention, in which detector modules are operationally deployed outside, rather than within, an enclosure 600, where, in this embodiment, the enclosure is a trailer that may be drawn to the site of operation behind a vehicle. FIG. 7 shows a rear view of the embodiment of FIG. 6.

Returning now to embodiments of the invention in which The relative motion of conveyance 10 and object 12 may be carefully controlled or may be monitored by sensor 18 which employs any of a variety of sensing methods, such as radar, ultrasound, or optical, including laser or LIDAR sensing, all provided as examples only, in order to sense the relative speed of conveyance 10 with respect to object 12. A signal provided by sensor 18 is employed by controller 40 in one or more of the following modalities:

The vehicle speed may be regulated, or, alternatively, the pixel registration may be corrected to compensate for vehicle speed anomalies so as to produce aspect-ratio-correct, distortion-free, backscatter x-ray images. Relevant techniques include but are not limited to:

Use of high precision speed-sensing devices to accurately measure vehicle speed at low (0.5 to 10 mile-per-hour) ranges;

low-speed (0.5 to 10 mile-per-hour) electronic and/or software-based engine and/or transmission controls;

custom vehicle drive-train gear design, which simultaneously produces low vehicle scan speed while maintaining the capability of offering roadworthy speed ranges, up to at least 55 miles per hour. In this context, the cruise-control system of a vehicle may be 'co-opted' to govern motion at low scanning speeds.

over/under-speed indications to the driver, using high-precision sensing devices coupled to a dashboard indicator, which the driver uses to manually adjust throttle and braking to maintain the desired vehicle speed within the range necessary to maintain distortion-free images;

friction drive for driving the wheels of the inspecting vehicle during inspection operations;

dynamic on-the-fly software correction. This method does not attempt to regulate vehicle speed but rather uses real-time high-precision vehicle speed and speed variation data from on-vehicle sensor(s), of which a tire-driven embodiment is designated by numeral 26, together with software algorithms which interpolate, average or in other ways correct for the aspect ratio distortion in the x-ray image data produced by off-speed or varying speed.

Remote sensing of the object's speed using one or more of a variety of sensors 18 and using signals generated by sensor 18 in software algorithms together with the vehicle speed data to effect dynamic aspect ratio correction of the backscatter x-ray image.

The foregoing methods for control and correction of relative motion variations may be used either singly or in combination, within the scope of the present invention. Sensors 18 may additionally provide for control of x-ray beam direction such that the relative speed and track angle of the source with respect to the scanned object may be actively tracked. This capability may advantageously allow improved images to be formed at faster speeds and, additionally, allow for relative motion that is not purely unidirectional. It should be noted, additionally, that in circumstances where no horizontal spatial resolution is required, detection of relative motion is obviated.

Figure 2:
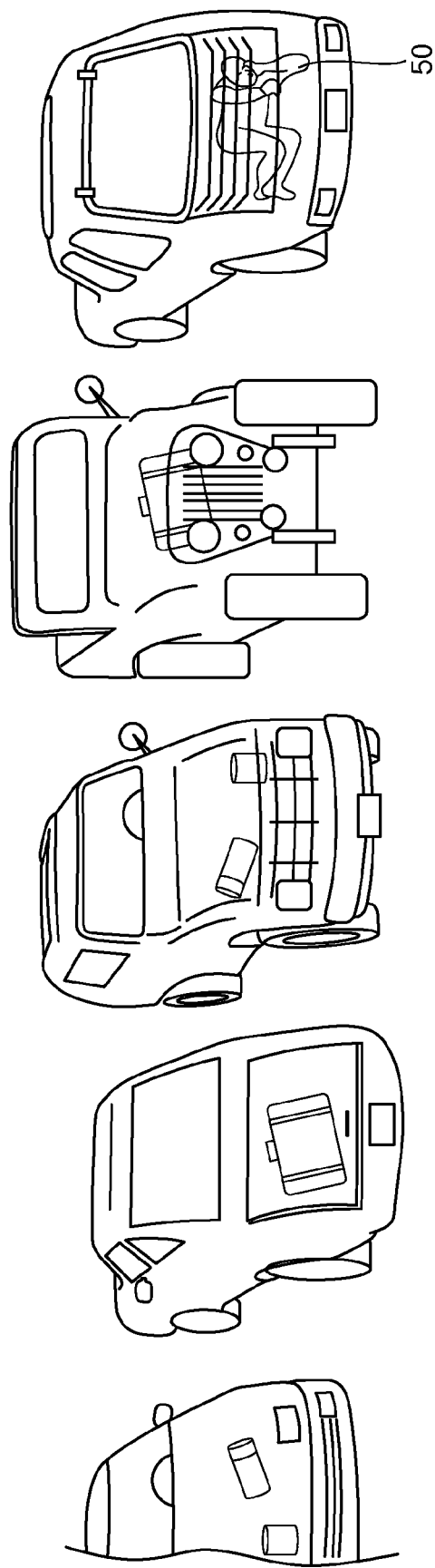
FIG. 2 is an image of various vehicles as imaged in backscatter radiation by the system of FIG. 1 in accordance with an embodiment of the invention.

FIG. 2 depicts a row of five vehicles scanned by a system as described in the present application, showing concealed contents of the vehicles in the various cases.

In the drive-by case, dosage to stationary people is readily reduced below regulatory thresholds provided vehicle speed is maintained above a specified minimum while x-rays are on. An interlock is provided to cut off x-ray generation when vehicle motion ceases or falls below a specified minimum speed. Otherwise, x-rays may be enabled regardless of proximity to objects.

For the stationary case, or for drive-by cases where additional safety measures are required or desired, proximity sensors, such as laser, microwave, ultrasound, or thermal sensors, for example, may be employed to determine the presence of objects to be scanned, enabling x-rays only when necessary, and/or to discern if humans are in the beam path. These sensors typically operate all the time, with their signals processed via software and/or hardware to intelligently control x-ray generation. The operator may also be provided with a manual "x-ray enable/deadman" control, in addition to any other safety devices and controls.

Features of the present invention may advantageously be employed in applications including, but not limited to, the following:

Inspection/manifest verification of containerized, palletized, or other packaged cargo, trucks or trailers being transported across or staged at ports, borders, air terminals, or similar transportation sites.

Verification that containers, objects, or vehicles are empty as claimed.

Inspection of vehicles attempting to enter controlled or high-value areas such as military bases, power plants, tunnels, air terminals, public or government buildings, parking garages, lobbies, service or delivery areas, tollbooths, or other important installations, for contraband or threats such as explosives, weapons, or smuggled personnel.

Inspection of vehicles or containers parked in garages, lots, or on public or private thoroughfares for explosives, weapons, contraband, or other threats.

Inspection of vehicles in motion for threats, contraband, or to verify contents.

Inspection of objects potentially containing radioactive materials that produce neutrons and or gamma rays.

Searching surrendering soldiers/civilians to ensure they are not wired.

Searching personnel at border crossings/checkpoints to screen out suicide bombers.

Scrutinizing persons in large groups.

The described embodiments of the invention are intended to be merely exemplary and numerous variations and modifications will be apparent to those skilled in the art. All such variations and modifications are intended to be within the scope of the present invention as defined in the appended claims.

We claim:

1. A method for employing penetrating radiation to inspect an object, the method comprising:

a. generating a beam of penetrating radiation originating entirely within the body of a static enclosure;

b. scanning the penetrating radiation across the object;

c. detecting penetrating radiation scattered by the object into the body of the enclosure by means of a detector module concealed within the enclosure and generating a scatter signal;

d. ascertaining a specified characteristic of the object based in part on the scatter signal; and e. generating a signal based on detection of any penetrating radiation naturally emitted by the object.

2. An inspection system for simultaneous active and passive inspection of an object by means of penetrating radiation, the system comprising:

a. a static imaging enclosure characterized by an enclosing body;

b. a source of penetrating radiation contained entirely within the body of the imaging enclosure for generating a beam of penetrating radiation; and c. a detector module, contained entirely within the body of the imaging enclosure, for generating a signal based both upon penetrating radiation scattered by contents of the object and any penetrating radiation naturally emitted by the contents.

3. An inspection system in accordance with claim 2, wherein the static imaging enclosure is a shipping container.

4. An inspection system in accordance with claim 2, further comprising an operator console for operation by an operator remotely disposed within a separate module coupled to the static imaging enclosure.

* * * * *